US00PP27946P2

(12) United States Plant Patent
Hartman

(10) Patent No.: US PP27,946 P2
(45) Date of Patent: Apr. 25, 2017

(54) ***CALADIUM* PLANT NAMED 'FLATTER ME'**

(50) Latin Name: *Caladium×hortulanum*
Varietal Denomination: Flatter Me

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 14/998,542

(22) Filed: Jan. 16, 2016

(51) Int. Cl.
*A01H 5/02* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Flatter Me', characterized by its intermediate height, upright and uniformly mounded plant habit; vigorous growth habit and moderately rapid growth rate; glossy fancy-type leaves with dark green background color with variable green and grey green-colored blotches and mottling and red to red purple-colored venation and areas surrounding the veins; and above average tolerance to *Xanthomonas* Leaf Spot.

4 Drawing Sheets

Botanical designation: *Caladium×hortulanum.*
Cultivar denomination: 'FLATTER ME'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Flatter Me'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2007 in Avon Park, Fla. of *Caladium×hortulanum* 'Mt. Everest', disclosed in U.S. Plant Pat. No. 18,764, as the female, or seed, parent with *Caladium×hortulanum* 'John Peed', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2008.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2009 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Flatter Me'. These characteristics in combination distinguish 'Flatter Me' as a new and distinct *Caladium* plant:

1. Intermediate in height, upright and uniformly mounded plant habit.
2. Vigorous growth habit and moderately rapid growth rate.
3. Glossy fancy-type leaves with dark green background color with variable green and grey green-colored blotches and mottling and red to red purple-colored venation and areas surrounding the veins.
4. Above average tolerance to *Xanthomonas* Leaf Spot.

Plants of the new *Caladium* differ primarily from plants of the female parent, 'Mt. Everest', in the following characteristics:

1. Plants of the new *Caladium* are shorter than plants of 'Mt. Everest'.
2. Plants of the new *Caladium* have fancy type leaves whereas plants of 'Mt. Everest' have strap (or lance) type leaves.
3. Leaves of plants of the new *Caladium* are glossy in luster whereas leaves of 'Mt. Everest' are mostly dull in luster.
4. Plants of the new *Caladium* and 'Mt. Everest' differ in leaf color as leaves of 'Mt. Everest' are creamy white to grey green in color with dark green-colored margins and cream to pinkish red-colored venation.

Plants of the new *Caladium* differ primarily from plants of the male parent, 'John Peed', in leaf color as leaves of 'John Peed' have dark red-colored centers and red-colored venation with dark green-colored margins.

Plants of the new *Caladium* can be compared to plants of *Caladium×hortulanum* 'Raspberry Moon', disclosed in U.S. Plant Pat. No. 20,069. In side-by-side comparisons, plants of the new *Caladium* differ primarily from plants of 'Raspberry Moon' in the following characteristics:

1. Plants of the new *Caladium* are shorter than plants of 'Raspberry Moon'.
2. Leaves of plants of the new *Caladium* are glossy in luster whereas leaves of 'Raspberry Moon' are mostly dull in luster.
3. Plants of the new *Caladium* and 'Raspberry Moon' differ in leaf color as leaves of 'Raspberry Moon' are lime green in color with random dark green and raspberry red-colored coalescing spots and splotches.

Plants of the new *Caladium* can be compared to plants of *Caladium×hortulanum* 'Frieda Hemple', not patented. In side-by-side comparisons, plants of the new *Caladium* differ primarily from plants of 'Frieda Hemple' in the following characteristics:

1. Leaves of plants of the new *Caladium* are glossy in luster whereas leaves of 'Frieda Hemple' are mostly dull in luster.
2. Plants of the new *Caladium* and 'Frieda Hemple' differ in leaf color as leaves of 'Frieda Hemple' are medium green in color with bright red-colored centers and venation.
3. Plant of the new *Caladium* and 'Frieda Hemple' differ in leaf petiole color as leaf petioles of 'Frieda Hemple' are dark brownish green, close to black, in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Flatter Me' in a container and grown in a shadehouse (tuber not de-eyed).

The photograph at the top of the second sheet is a comparison view of typical potted plants of the female parent, 'Mt. Everest' (right), 'Flatter Me' (center) and the male parent, 'John Peed' (left).

The photograph at the bottom of the second sheet is a comparison view of typical potted plants of 'Frieda Hemple' (left), 'Flatter Me' (center) and 'Raspberry Moon' (right).

The photograph at the top of the third sheet is a comparison view of typical plants of 'Flatter Me' grown in containers; the plant on the left has not had its tuber de-eyed and the plant on the right has had its tuber de-eyed prior to planting.

The photograph at the bottom of the third sheet is a side perspective view of typical plants of 'Flatter Me' grown in an open field.

The photograph on the fourth sheet is a close-up view of typical freshly-harvested tubers and roots of 'Flatter Me'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were eleven weeks old and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Flatter Me'.

Parentage:

*Female, or seed, parent.*—*Caladium×hortulanum* 'Mt. Everest', disclosed in U.S. Plant Pat. No. 18,764.

*Male, or pollen, parent.*—*Caladium×hortulanum* 'John Peed', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description (outdoor nursery-grown plants).*—Appearance: Multi-segmented and somewhat flattened; individual segments ovate to elliptic in shape. Height: About 3 cm. Diameter: About 4.2 cm to 6.2 cm. Segment height: About 2 cm to 2.9 cm. Segment diameter: About 2.3 cm to 2.7 cm. Axillary buds, height: About 5 mm. Texture: Thick, starchy. Color: Epidermis, freshly-harvested: Close to 159C to 159D; outer skin, close to 199B to 199C. Epidermis, dried: Close to 200A. Cortical tissue: Close to 8D. Axillary buds: Close to 155D and 164D. Root description: Thick, fleshy contractile roots; color, close to 155C and 199A. Rooting habit: Medium density.

Plant description:

*Plant type.*—Herbaceous perennial; suitable as a potted plant in containers 15-cm to 25-cm and suitable as a landscape plant in shaded areas.

*Plant and growth habit.*—Intermediate in height, upright and uniformly mounded plant habit; vigorous and dense growth habit; moderately rapid growth rate, potted plants in finished or saleable form in about eleven weeks after planting tubers; leaf petioles and leaves arise from one or more growing points on tubers; petioles mostly upright and outwardly leaning with development.

*Plant height, from soil level to top of foliar plane, shadehouse-grown potted plants.*—About 30 cm to 39 cm.

*Plant diameter or spread, shadehouse-grown potted plants.*—About 35 cm to 41 cm.

*Number of shoots per plant, shadehouse-grown potted plants, tubers not de-eyed.*—About two to three develop per #1 tuber.

*Number of shoots per plant, shadehouse-grown potted plants, tubers de-eyed.*—About three to four develop per #1 tuber.

*Cataphylls, shadehouse-grown potted plants.*—Length: About 4 cm to 5.5 cm. Width: About 1 cm to 1.5 cm. Shape: Narrowly elliptic. Apex: Acute. Base: Sheathing the stem. Color, inner surface: Close to 155C; colors and patterns on the outer surface are visible on the inner surface. Color, outer surface: Close to 159C and 182D tinged with close to 147C; stippled, streaked and tessellated with close to 200B tinged with close to 147B; with development, color becoming closer to 200D.

Leaf description:

*Arrangement and type.*—Alternate; simple; fancy-type.

*Length, shadehouse-grown potted plants.*—About 16 cm to 25 cm.

*Width, shadehouse-grown potted plants, flattened.*—About 11.5 cm to 18 cm.

*Shape.*—Ovate, cordate.

*Apex.*—Acute.

*Base.*—Sagittate to peltate.

*Margin.*—Entire; mostly flat or slightly undulate.

*Texture, upper and lower surfaces.*—Smooth, glabrous.

*Luster, upper surface.*—Glossy.

*Luster, lower surface.*—Glaucous, dull sheen.

*Venation pattern.*—Pinnate.

*Color, shadehouse-grown potted plants.*—Developing leaves, upper surface: Background color: Close to 147A. Midvein and primary venation: Close to 187B. Areas surrounding venation: Close to 187C and 183A. Interveinal areas: Blotches and mottling, close to 146B to 146C, 194B, 194C and 194D. Margins: Close to 147A. Basal notch: Close to 187B. Point of petiole attachment: Close to N186C. Developing leaves, lower surface: Background color: Close to 191A tinged with close to 189A. Midvein and primary venation: Close to 182B. Areas surrounding venation: Close to 186A and 185C. Interveinal areas: Close to 193A and close to 191A tinged with close to 189A. Margins: Close to 187A. Basal notch: Close to 187B. Point of petiole attachment: Close to N186C. Fully expanded leaves, upper surface: Background color: Close to 147A. Midvein and primary venation: Close to 187B. Areas surrounding venation: Close to 187C, 183A and 184A. Interveinal areas: Blotches and mottling, close to 146B to 146C, 195C, 196B and 194B to 194C. Margins: Close to 147A. Basal notch: Close to N186C. Fully expanded leaves, lower surface: Background color: Close to 191 A tinged with close to 189A. Midvein and primary venation: Close to 182B to 182C; distally, close to 147C. Areas surrounding venation: Close to 186A and 185C. Interveinal areas: Close to 193A to 193B, close to 191B and close to 191A tinged with close to 189A. Margins: Close to 187A. Basal notch: Close to N186C.

*Petioles.*—Aspect: Initially upright and straight; with development, outwardly leaning; flexible. Length, shadehouse-grown potted plants: About 18 cm to 27 cm. Diameter, distally, shadehouse-grown potted plants: About 3.5 mm to 4 mm. Diameter, proximally, shadehouse-grown potted plants: About 5 mm to 8 mm. Texture: Smooth, glabrous; glaucous. Color, shadehouse-grown potted plants: Close to N170D, 177D and 182D, streaked, tessellated and stippled with close to 200B and 177A; below the leaf and petiole junction, close to N170D and 182D. Wing length, shadehouse-grown potted plants: About 3 cm to 4.5 cm. Wing diameter, shadehouse-grown potted plants: About 5 mm to 8 mm. Texture, inner and outer surfaces: Smooth, glabrous. Luster, inner and outer surfaces: Dull to slightly glossy. Wing color, shadehouse-grown potted plants: Inner surface: Close to N155C; colors and patterns on the outer surface are visible on the inner surface. Outer surface: Close to 159C and close to 182D tinged with close to 147C, stippled, streaked and tessellated with close to 200B tinged with close to 147B.

Inflorescence description: Inflorescence initiation and development have not been observed on plants of the new *Caladium.*

Disease & pest tolerance: Plants of the new *Caladium* have been observed to have above average tolerance to *Xanthomonas* Leaf Spot and average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Flatter Me' as illustrated and described.

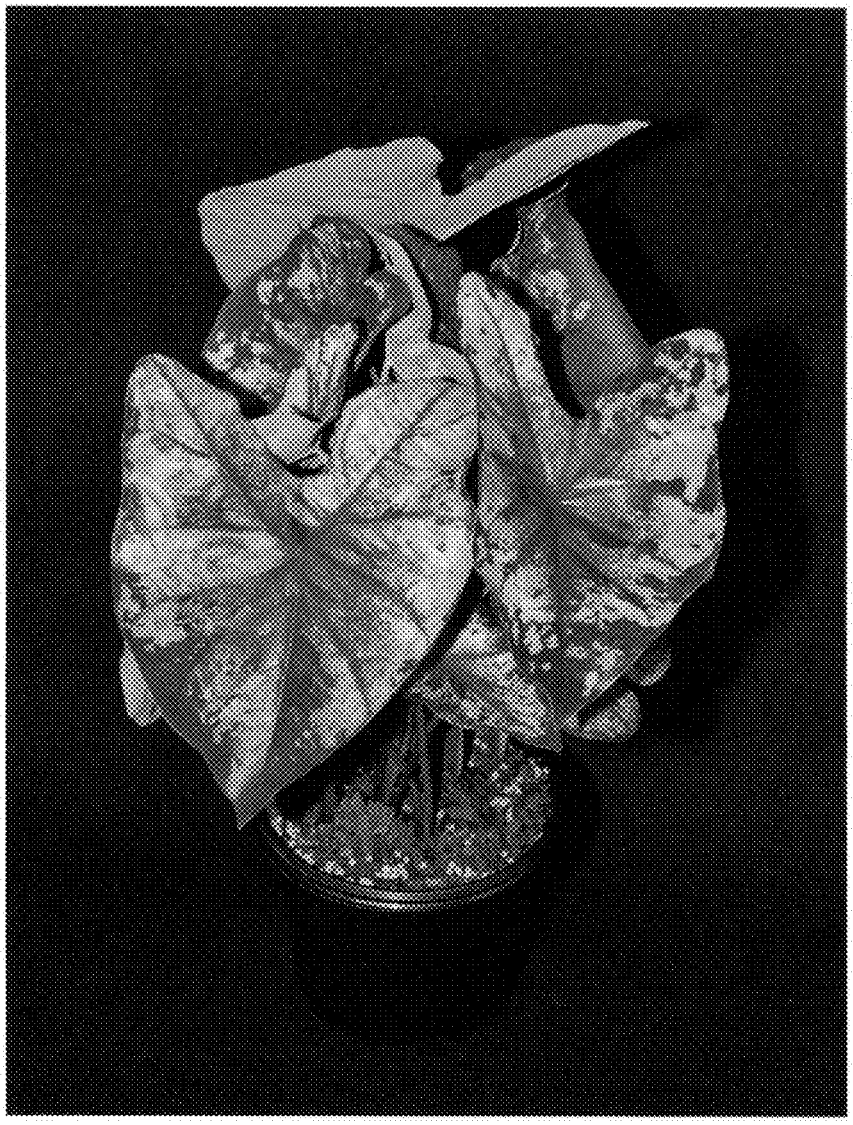

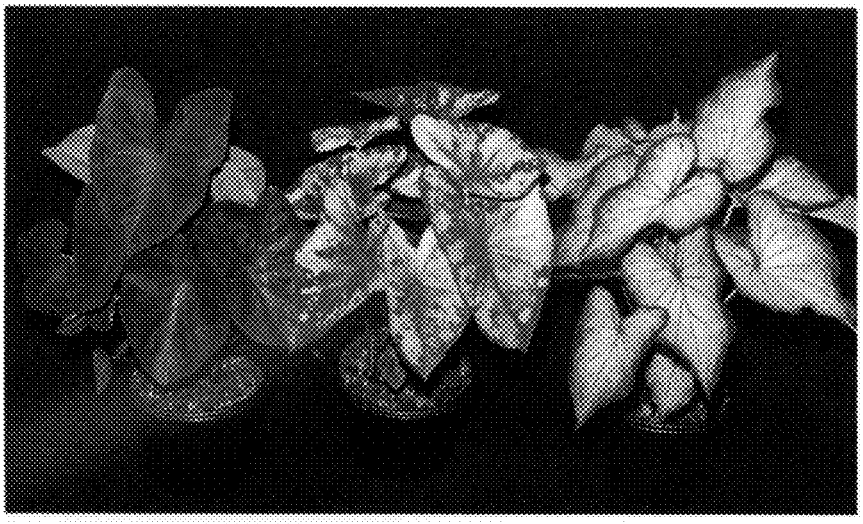
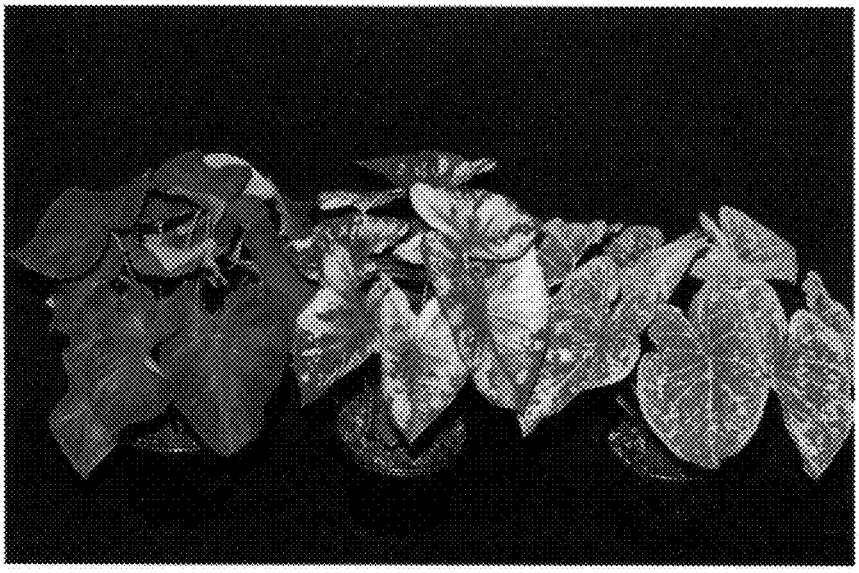

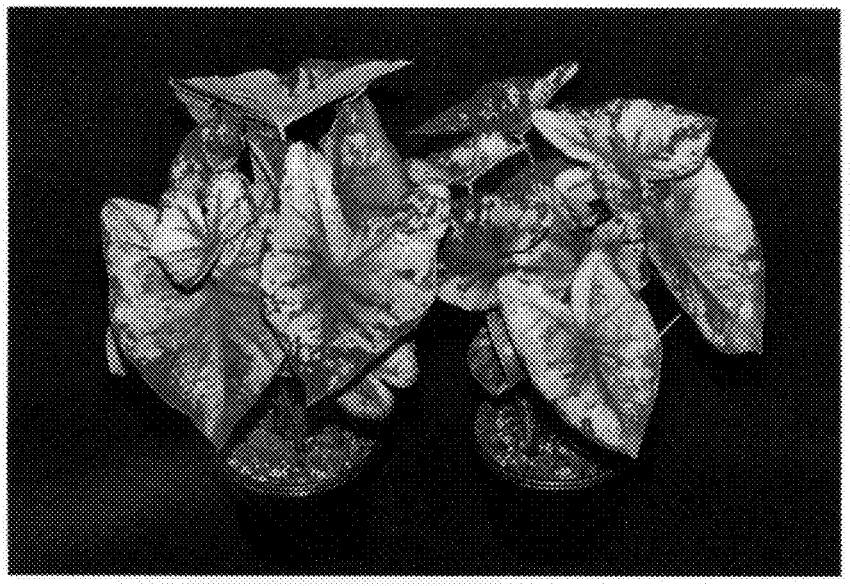
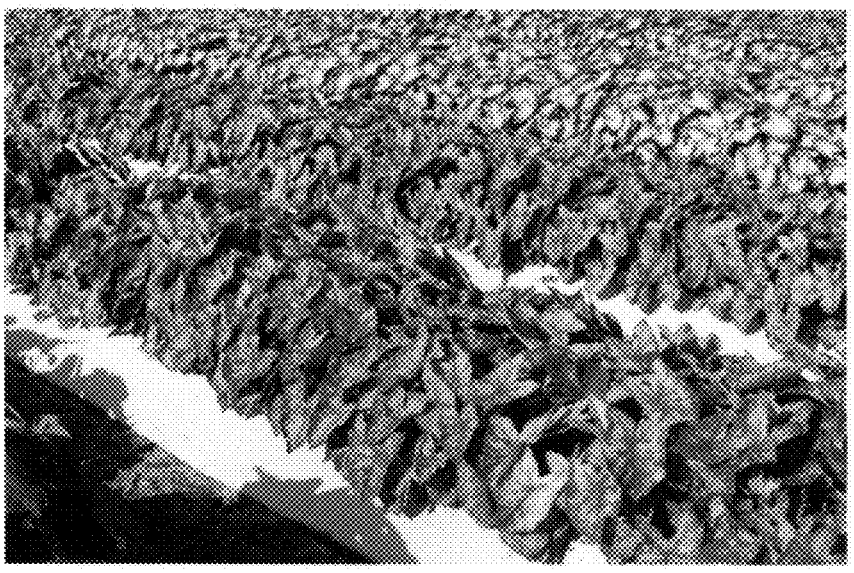

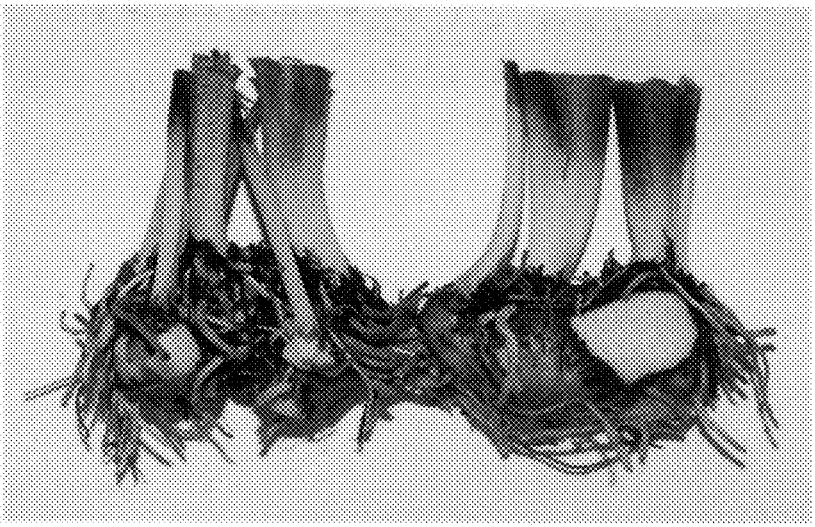

* * * * *